(12) United States Patent
Atkinson (10) Patent No.: US 8,817,040 B2
(45) Date of Patent: Aug. 26, 2014

(54) METHODS FOR ENHANCING IMAGE QUALITY

(75) Inventor: Roscoe Atkinson, San Juan Capistrano, CA (US)

(73) Assignee: Carl Zeiss Microscopy GmbH, Jena (DE)

( * ) Notice: Subject to any disclaimer, the term of this patent is extended or adjusted under 35 U.S.C. 154(b) by 911 days.

(21) Appl. No.: 12/454,711

(22) Filed: May 21, 2009

(65) Prior Publication Data

US 2010/0021077 A1 Jan. 28, 2010

Related U.S. Application Data (63) Continuation of application No. 11/520,444, filed on Sep. 12, 2009, now abandoned.

(60) Provisional application No. 60/716,887, filed on Sep. 13, 2005.

(51) Int. Cl.
*G09G 5/02* (2006.01)
*G06K 9/40* (2006.01)
*G01J 3/46* (2006.01)

(52) U.S. Cl.
CPC . *G09G 5/02* (2013.01); *G01J 3/462* (2013.01); *G01J 3/463* (2013.01); *G01J 2003/467* (2013.01); *G06T 2207/10036* (2013.01); *G06T 2207/10056* (2013.01)
USPC .......... 345/604; 345/600; 345/601; 345/602; 345/603; 382/274; 358/1.9

(58) Field of Classification Search
CPC ............ G09G 2340/06; G06T 11/001; G06T 2207/10036; G06T 2207/10056; G01J 2003/467; G01J 3/462; G01J 3/463

USPC ........... 382/128–132, 274; 358/1.9; 345/604, 345/600, 601, 602, 603
See application file for complete search history.

(56) References Cited

U.S. PATENT DOCUMENTS

| | | | |
|---|---|---|---|
| 3,824,393 A | 7/1974 | Brain | |
| 3,851,972 A | 12/1974 | Smith et al. | |
| 4,011,004 A | 3/1977 | Levine et al. | |
| 4,090,243 A | 5/1978 | Kotera et al. | |

(Continued)

FOREIGN PATENT DOCUMENTS

| | | |
|---|---|---|
| EP | 0 557 871 A2 | 9/1993 |
| EP | 0 713 086 A1 | 5/1996 |

(Continued)

OTHER PUBLICATIONS

U.S. Appl. No. 11/520,444, filed Sep. 12, 2006.

(Continued)

*Primary Examiner* — Jin-Cheng Wang
(74) *Attorney, Agent, or Firm* — Patterson Thuente Pedersen, P.A.

(57) ABSTRACT

A magnified image is improved by integrating the wavelength specific component into that image. A magnified images obtained, and at least one wavelength specific component images also obtained. The different images are converted in color space, and different channels, indicative of the different parts of the image shows, are also obtained. For example, the image may be converted to an L*a*b* color space, and the luminance channel of the wavelength specific component may be used to enhance or replace the luminance channel of the magnified image.

8 Claims, 5 Drawing Sheets

(56) References Cited

U.S. PATENT DOCUMENTS

| | | | |
|---|---|---|---|
| 4,125,828 | A | 11/1978 | Resnick et al. |
| 4,249,825 | A | 2/1981 | Shapiro |
| 4,393,466 | A | 7/1983 | Deindoerfer et al. |
| 4,513,438 | A | 4/1985 | Graham et al. |
| 4,673,973 | A | 6/1987 | Ledley |
| 4,700,298 | A | 10/1987 | Palcic et al. |
| 4,718,089 | A | 1/1988 | Hayashi et al. |
| 4,740,270 | A | 4/1988 | Roy |
| 4,902,101 | A | 2/1990 | Fujihara et al. |
| 4,991,223 | A | 2/1991 | Bradley |
| 5,016,173 | A | 5/1991 | Kenet et al. |
| 5,085,325 | A | 2/1992 | Jones et al. |
| 5,087,965 | A | 2/1992 | Torre-Bueno |
| 5,088,817 | A | 2/1992 | Igaki et al. |
| 5,202,931 | A | 4/1993 | Bacus |
| 5,231,580 | A | 7/1993 | Cheung et al. |
| 5,233,684 | A | 8/1993 | Ulichney |
| 5,241,468 | A | 8/1993 | Kenet |
| 5,257,182 | A | 10/1993 | Luck et al. |
| 5,281,517 | A | 1/1994 | Bacus et al. |
| 5,287,272 | A | 2/1994 | Rutenberg et al. |
| 5,317,140 | A | 5/1994 | Dunthorn |
| 5,321,545 | A | 6/1994 | Bisconte |
| 5,375,177 | A | 12/1994 | Vaidyanathan et al. |
| 5,400,081 | A | 3/1995 | Chaplin |
| 5,409,007 | A | 4/1995 | Saunders et al. |
| 5,420,042 | A | 5/1995 | Schafer et al. |
| 5,428,690 | A | 6/1995 | Bacus et al. |
| 5,432,865 | A | 7/1995 | Kasdan et al. |
| 5,432,871 | A | 7/1995 | Novik |
| 5,449,622 | A | 9/1995 | Yabe et al. |
| 5,463,470 | A | 10/1995 | Terashita et al. |
| 5,473,706 | A | 12/1995 | Bacus et al. |
| 5,481,401 | A | 1/1996 | Kita et al. |
| 5,499,097 | A | 3/1996 | Ortyn et al. |
| 5,515,172 | A | 5/1996 | Shiau |
| 5,526,258 | A | 6/1996 | Bacus |
| 5,533,628 | A | 7/1996 | Tao |
| 5,583,666 | A | 12/1996 | Ellson et al. |
| 5,585,469 | A | 12/1996 | Kojima et al. |
| 5,602,937 | A | 2/1997 | Bedrosian et al. |
| 5,602,941 | A | 2/1997 | Charles et al. |
| 5,625,705 | A | 4/1997 | Recht |
| 5,635,402 | A | 6/1997 | Alfano et al. |
| 5,647,025 | A | 7/1997 | Frost et al. |
| 5,671,288 | A | 9/1997 | Wilhelm et al. |
| 5,691,779 | A | 11/1997 | Yamashita et al. |
| 5,701,172 | A | 12/1997 | Azzazy |
| 5,706,093 | A | 1/1998 | Komiya |
| 5,717,518 | A | 2/1998 | Shafer et al. |
| 5,732,150 | A | 3/1998 | Zhou et al. |
| 5,734,498 | A | 3/1998 | Krasieva et al. |
| 5,783,814 | A | 7/1998 | Fairley et al. |
| 5,795,723 | A | 8/1998 | Tapscott et al. |
| 5,799,105 | A | 8/1998 | Tao |
| 5,846,749 | A | 12/1998 | Slamon et al. |
| 5,907,315 | A | 5/1999 | Vlahos et al. |
| 5,911,003 | A | 6/1999 | Sones |
| 5,911,327 | A | 6/1999 | Tanaka et al. |
| 5,937,104 | A | 8/1999 | Henderson et al. |
| 5,981,279 | A | 11/1999 | Weiss |
| 6,005,964 | A | 12/1999 | Reid et al. |
| 6,007,996 | A | 12/1999 | McNamara et al. |
| 6,011,595 | A | 1/2000 | Henderson et al. |
| 6,031,930 | A | 2/2000 | Bacus et al. |
| 6,034,794 | A | 3/2000 | Suganuma |
| 6,058,322 | A | 5/2000 | Nishikawa et al. |
| 6,061,425 | A | 5/2000 | Sato |
| 6,101,265 | A | 8/2000 | Bacus et al. |
| 6,103,479 | A | 8/2000 | Taylor |
| 6,103,518 | A | 8/2000 | Leighton |
| 6,104,830 | A | 8/2000 | Schistad |
| 6,104,839 | A | 8/2000 | Cok et al. |
| 6,122,400 | A | 9/2000 | Reitmeier |
| 6,151,405 | A | 11/2000 | Douglass et al. |
| 6,165,734 | A | 12/2000 | Garini et al. |
| 6,183,981 | B1 | 2/2001 | Gonzalez-Lima |
| 6,208,753 | B1 | 3/2001 | Braudaway et al. |
| 6,215,892 | B1 | 4/2001 | Douglass et al. |
| 6,219,446 | B1 | 4/2001 | Kiriki et al. |
| 6,226,392 | B1 | 5/2001 | Bacus et al. |
| 6,251,586 | B1 | 6/2001 | Mulshine et al. |
| 6,272,247 | B1 | 8/2001 | Manickam et al. |
| 6,288,703 | B1 | 9/2001 | Berman et al. |
| 6,301,382 | B1 | 10/2001 | Smith et al. |
| 6,313,452 | B1 | 11/2001 | Paragano et al. |
| 6,404,906 | B2 | 6/2002 | Bacus et al. |
| 6,404,916 | B1 | 6/2002 | De La Torre-Bueno |
| 6,418,236 | B1 | 7/2002 | Ellis et al. |
| 6,424,421 | B1 | 7/2002 | Cremer et al. |
| 6,453,060 | B1 | 9/2002 | Riley et al. |
| 6,456,734 | B1 | 9/2002 | Youvan et al. |
| 6,499,690 | B1 | 12/2002 | Katayama et al. |
| 6,504,953 | B1 | 1/2003 | Behrends |
| 6,522,774 | B1 | 2/2003 | Bacus et al. |
| 6,542,187 | B1 | 4/2003 | Hamilton, Jr. et al. |
| 6,553,135 | B1 | 4/2003 | Ring et al. |
| 6,587,224 | B1 | 7/2003 | Nabeshima et al. |
| 6,611,289 | B1 | 8/2003 | Yu et al. |
| 6,674,884 | B2 | 1/2004 | Bacus et al. |
| 6,674,896 | B1 | 1/2004 | Torre-Bueno |
| 6,697,509 | B2 | 2/2004 | De La Torre-Bueno |
| 6,697,522 | B1 | 2/2004 | Ishikawa |
| 6,716,588 | B2 | 4/2004 | Sammak et al. |
| 6,716,974 | B1 | 4/2004 | Maciag et al. |
| 6,727,225 | B2 | 4/2004 | Wiley |
| 6,942,970 | B2 | 9/2005 | Isola et al. |
| 7,065,236 | B2 | 6/2006 | Marcelpoil et al. |
| 7,180,642 | B2 | 2/2007 | Miyatake |
| 7,339,699 | B1 | 3/2008 | Suzuki et al. |
| 2001/0036304 | A1* | 11/2001 | Yang et al. .......... 382/132 |
| 2002/0141640 | A1 | 10/2002 | Kraft |
| 2003/0017491 | A1 | 1/2003 | Shi et al. |
| 2003/0031375 | A1 | 2/2003 | Enomoto |
| 2003/0053690 | A1 | 3/2003 | Trifonov et al. |
| 2003/0138140 | A1 | 7/2003 | Marcelpoil et al. |
| 2004/0017586 | A1 | 1/2004 | Nichogi |
| 2004/0114227 | A1 | 6/2004 | Henderson et al. |
| 2004/0209178 | A1 | 10/2004 | Itakura et al. |
| 2005/0100189 | A1 | 5/2005 | Yamada |
| 2005/0111017 | A1* | 5/2005 | Takahashi et al. .......... 358/1.9 |
| 2005/0114801 | A1 | 5/2005 | Yang et al. |
| 2005/0180628 | A1 | 8/2005 | Curry et al. |
| 2006/0041385 | A1 | 2/2006 | Bauer et al. |
| 2006/0178833 | A1 | 8/2006 | Bauer et al. |
| 2007/0029462 | A1 | 2/2007 | Perz et al. |
| 2007/0091109 | A1 | 4/2007 | Atkinson |
| 2007/0092135 | A1 | 4/2007 | Piirainen |
| 2008/0260218 | A1* | 10/2008 | Smith et al. .......... 382/128 |

FOREIGN PATENT DOCUMENTS

| | | |
|---|---|---|
| WO | WO 92/17848 | 10/1992 |
| WO | WO 97/20198 | 6/1997 |
| WO | WO 01/29265 A1 | 4/2001 |
| WO | WO 01/46657 A1 | 6/2001 |
| WO | WO 01/51928 A1 | 7/2001 |
| WO | WO 03/025554 A2 | 3/2003 |
| WO | WO 2005/036877 A1 | 4/2005 |

OTHER PUBLICATIONS

Russ, "The Image Processing Handbook, Chapter 3—Correcting Imaging Defects" Third Edition, 1999, pp. 161-225.

Russ, "The Image Processing Handbook, Chapter 4—Image Enhancement Processing in the Spatial Domain", Third Edition, 1999, pp. 227-303.

\* cited by examiner

Breast Cancer Her2 60X

FIG 5A

Original

FIG 5C

FIG 5B 720 nm enhanced

FIG 5D

METHODS FOR ENHANCING IMAGE QUALITY

This application is a continuation of application Ser. No. 11/520,444, filed Sep. 12, 2006, which in turn claims priority to U.S. Provisional Application Ser. No. 60/716,887, filed on Sep. 13, 2005. Each of the aforementioned applications is hereby fully incorporated herein by reference.

BACKGROUND

Pathology often requires viewing microscope images. The resolution of the microscope images from the imaging system. This is often limited by different parameters of obtaining the image. For example, the resolution may be limited by the time it takes to scan a tissue section and by the resulting image file size.

DETAILED DESCRIPTION

The general structure and techniques, and more specific embodiments which can be used to effect different ways of carrying out the more general goals, are described herein.

The number of image elements within an obtained image from a tissue section increases exponentially between different microscope objectives. For example, the image at 10× may require exponentially more storage than the image at 4×. The time that is required to scan the tissue section at 60× may be excessive. Therefore, many believe that capturing a large image at 60× is not practical. The time required to scan a tissue section at 60× is extremely large, and the amount of digital storage space required for such a scan is also large. This may limit the number of scans that can be obtained and reviewed.

An embodiment describes use of a multi spectral imaging system, such as the Nuance Multispectral Imaging System available from Cambridge Research & Instrumentation ("Nuance") in combination with an automated microscope such as the Automated Cellular Imaging System ("ACIS") provided by Clarient Inc. The processing provides an effective augmentation of images at lower magnifications, to attempt to obtain additional information from those images at lower magnifications. In an embodiment, image augmentation is carried out by extracting images at specific color wavelengths, converting color spaces, and carrying out channel mixing in a converted color space.

Figure 2:
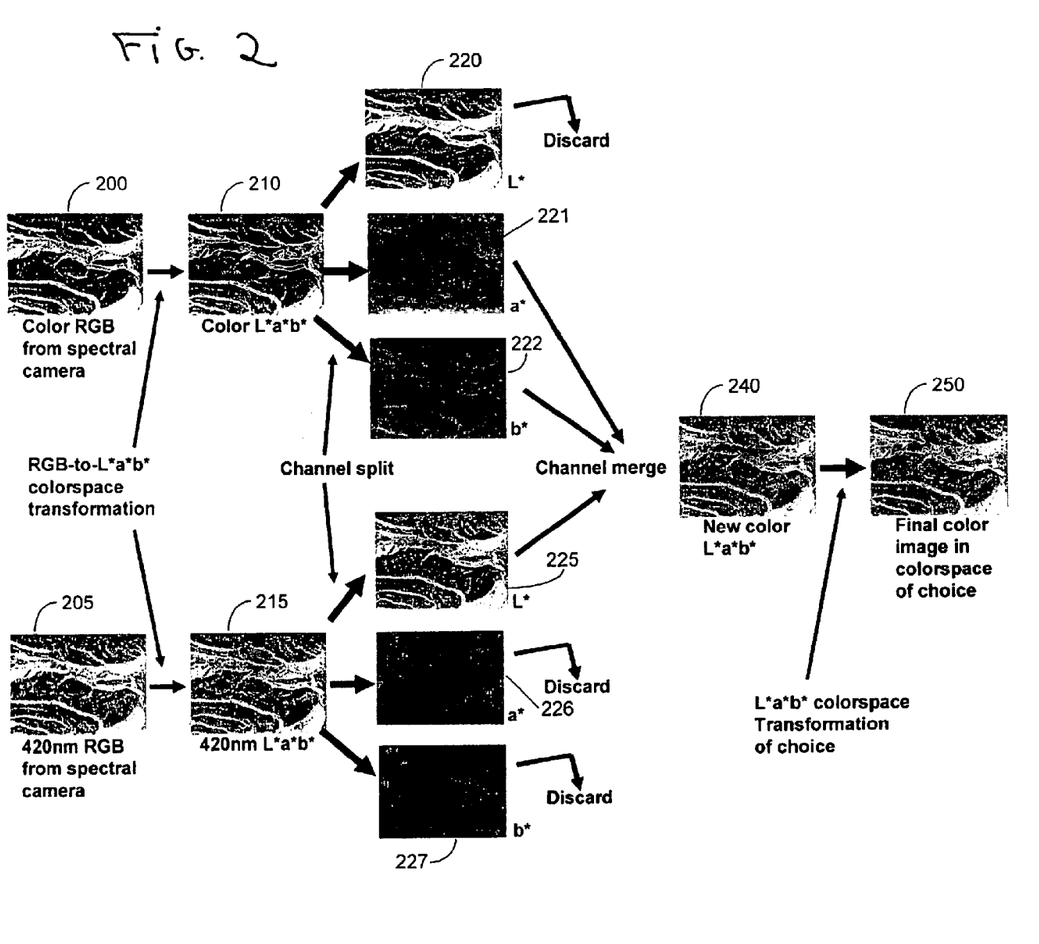
FIG. 2 illustrates the progression of the different images.
Figure 3:
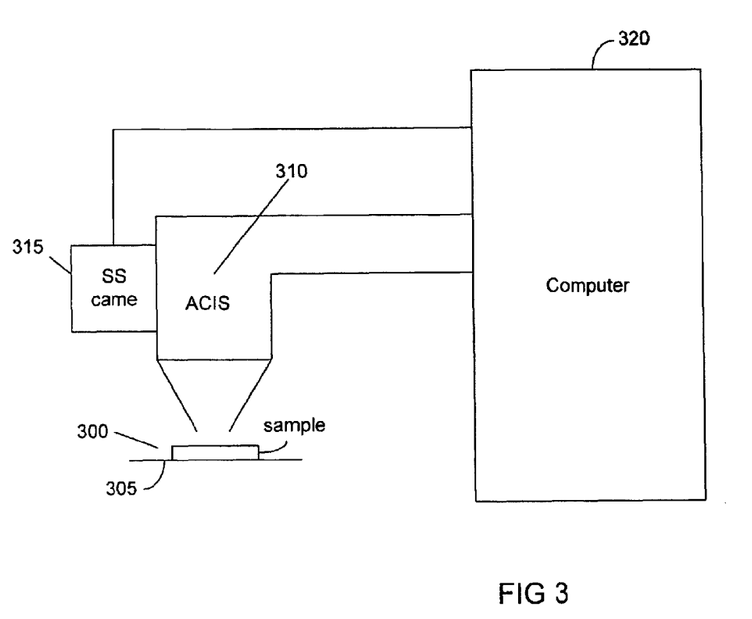
FIG. 3 illustrates an exemplary hardware setup which can be used.

FIG. 3 illustrates an exemplary hardware setup which can be used. The sample 300 is on a sample table 305 as conventional. The ACIS or other automated microscope 310 obtains image information from the sample 300. A single spectrum camera 315 also obtains information. All of the information is coupled to a computer 320 which operates as described herein and specifically according to the flowcharts of FIGS. 1 and 2.

A color space is a model for representing color in terms of intensity values; a color space specifies how color information is represented. It defines a one, two, three, or four-dimensional space whose dimensions, or components, represent intensity values. A color component is also referred to as a color channel. For example, RGB space is a three-dimensional color space whose components are the red, green, and blue intensities that make up a given color. Visually, these spaces are often represented by various solid shapes, such as cubes, cones, or polyhedral.

Different kinds of color spaces are known.

Gray spaces typically have a single component, ranging from black to white. The RGB space is a three-dimensional color space whose components are the red, green, and blue intensities that make up a given color. For example, scanners read the amounts of red, green, and blue light that are reflected from an image and then convert those amounts into digital values. Displays receive the digital values and convert them into red, green, and blue light seen on a screen.

RGB-based color spaces are the most commonly used color spaces in computer graphics, primarily because they are directly supported by most color displays and scanners. RGB color spaces are device dependent and additive. The groups of color spaces within the RGB base family include HSV (hue, saturation, value) and HLS (hue, lightness, saturation) spaces. The saturation component in both color spaces describes color intensity. A saturation value of 0 (in the middle of a hexagon) means that the color is "colorless" (gray); a saturation value at the maximum (at the outer edge of a hexagon) means that the color is at maximum "colorfulness" for that hue angle and brightness. The value component (in HSV space) and the lightness component (in HLS space) describe brightness or luminance. In both color spaces, a value of a represents black. In HSV space, a maximum value means that the color is at its brightest. In HLS space, a maximum value for lightness means that the color is white, regardless of the current values of the hue and saturation components. The brightest, most intense color in HLS space occurs at a lightness value of exactly half the maximum.

CMY color spaces are like the above, but define the colors additively.

Any color expressed in RGB space is some mixture of three primary colors: red, green, and blue. Most RGB-based color spaces can be visualized as a cube, with corners of black, the three primaries (red, green, and blue), the three secondaries (cyan, magenta, and yellow), and white.

Some color spaces can express color in a device-independent way. Whereas RGB colors vary with display and scanner characteristics, and CMYK colors vary with printer, ink, and paper characteristics, device-independent colors are meant to be true representations of colors as perceived by the human eye. These color representations, called device-independent color spaces, result from work carried out in 1931 by the Commission Internationale d'Eclairage (CIE), and for that reason are also called CIE-based color spaces.

In the L*a*b color space, the L*a*b* space consists of a luminosity 'L*' or brightness layer, chromaticity layer 'a*' indicating where color falls along the red-green axis, and chromaticity layer 'b*' indicating where the color falls along the blue-yellow axis.

An embodiment is described herein. The embodiment can be carried out automatically using a robotic or computer-controlled system. Alternatively, some parts of the embodiment, such as the staining or the input of data into machines, can be carried out manually.

Figure 1:
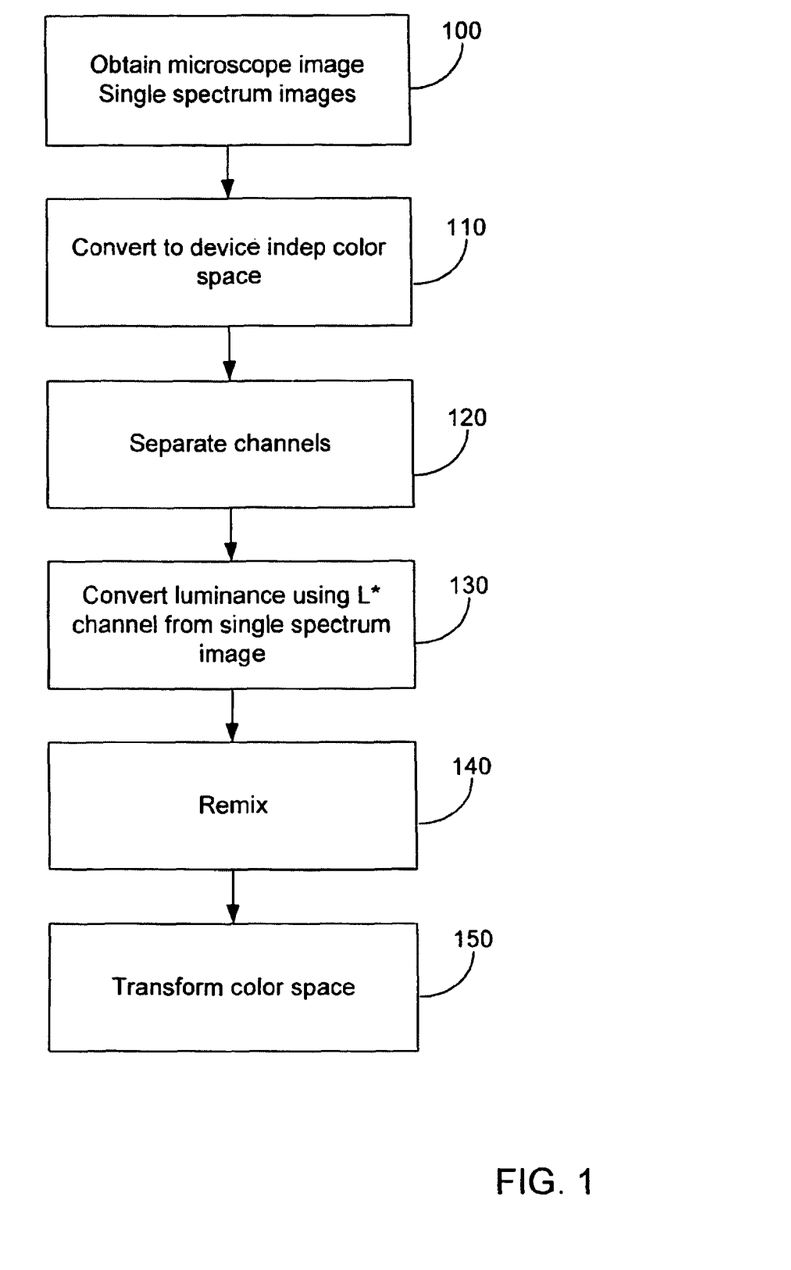
FIG. 1 shows a flowchart.

At 100, the system obtains a number of different images, including a first microscopic image, and at least one single spectrum image. Preferably, a plurality of different single spectrum images are obtained. FIG. 2 also illustrates the different images, including the color image 200 from the microscope or from the spectral camera, and a single spectrum image 205 from the spectral camera.

Colon cancer tissue sections may be examined in this embodiment. These sections are in fixed paraffin and stained with HER2 stain. A multispectral camera, which in the embodiment can be the Nuance camera, is used to examine the tissue sections. The Nuance camera is mounted on an ACIS microscope.

For purposes of the embodiment, color RGB images are obtained at any magnification, e.g., 4×, 10×, 20× and/or 60×. Grayscale images of the exact same fields are also captured at near ultraviolet (420 nm) and near infrared (720 nm). Physics dictates that resolution is inversely proportional to wavelength. One would therefore predict that the 420 nm image would have better resolution than any of the RGB channels of the original color images.

The images obtained from the cameras are in an RGB based color space. At 110, the images are converted into a device independent color space which includes a luminance component. More specifically, in the embodiment, the devices are converted into the L*a*b* color space. FIG. 2 shows the image 200 being converted into the new color space image 210, and the image 205 being converted into the new color space image 215. This color space conversion may use commercially available software or modules.

At 120, the channels of the new images are separated. In FIG. 2, image 210 is divided into seperated channels, the L* channel 220, the a* channel 221 and the b* channel 222. Similarly, the image 215 is converted into its separate channels representing separate image parts, 225, 226 and 227.

In the embodiment, only the luminance information from the single spectrum image 205 is used. Accordingly, at 130, the luminance channels from the image 200 are replaced by the luminance channel from their corresponding 420 nm image 205. The channels are then premixed at 140 to create the image 240, and then are transformed back to another color space transformation at 150 such as RGB, HSI, or any other color space of a type that may facilitate the display.

According to the embodiment, it was found that the new image provided more detail than the original. In order to test the importance of the 420 nm image, the same process was done using a 720 nm spectral image in place of the 420 nm image. The resulting images were of poor quality.

Another embodiment tested immunohistochemical stained tissue. This tissue test was a breast-cancer test tissue stained with Her2/neu, using diainobenzidine ("DAB") secondary, and a hematoxylin counterstain. Surprisingly, this process increased the detail of the hematoxylin stained counterstain tissue but greatly reduced the information carried by the stained cancer tissue, which became less interpretable.

The inventor believes that the brown DAB based secondary stain contains a great deal of red color. Therefore, the 720 nm process was applied with very good results. The DAB stained tissue showed an increase detail at ends the background of slightly decreased background detail.

Figure 4A:
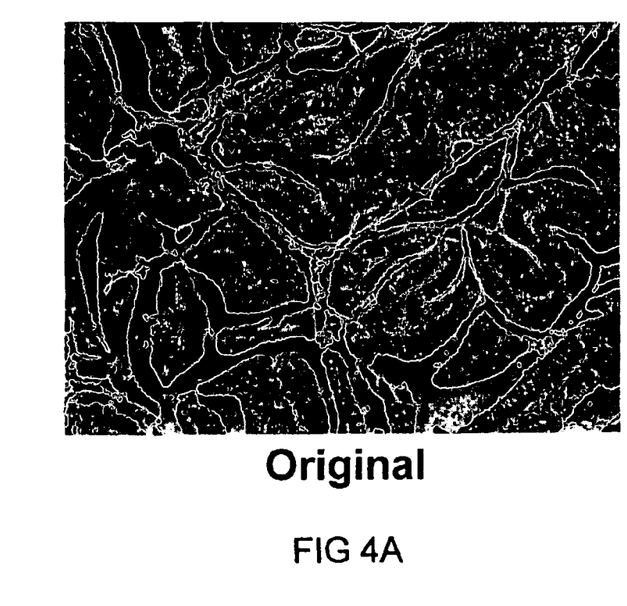
FIGS. 4a and 4b show examples of the different images for colon cancer.
Figure 4B:
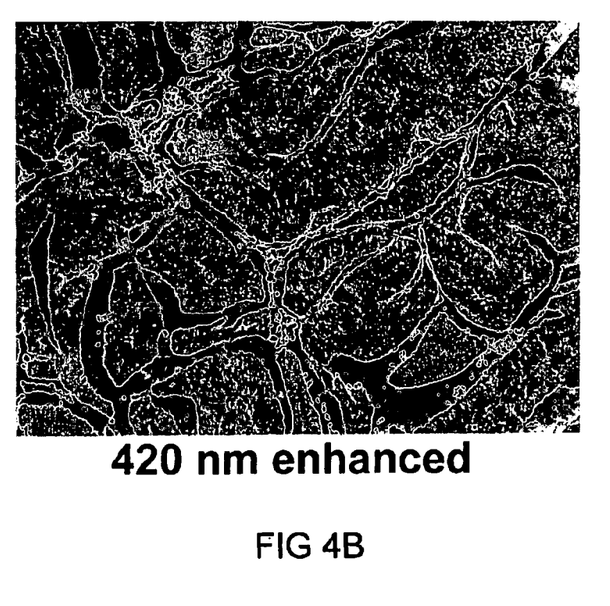
Figure 5A:
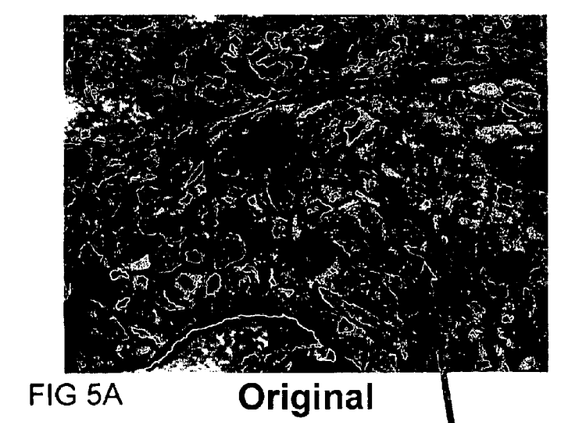
FIGS. 5a through 5d show examples of the different images for a breast cancer cell.
Figure 5B:
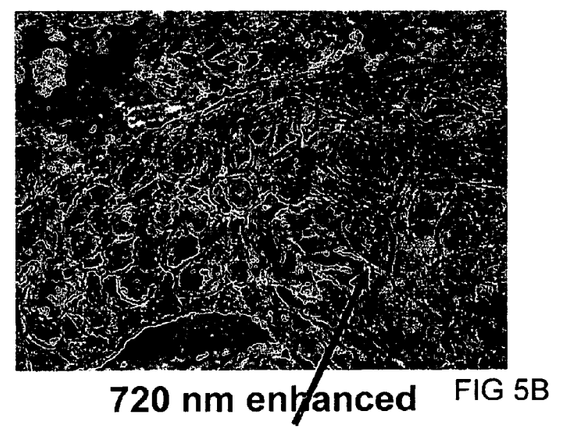
Figure 5C:
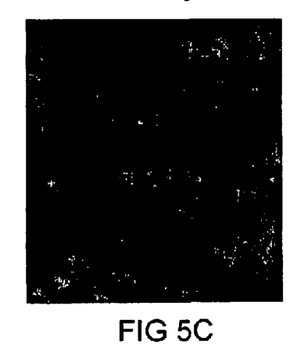
Figure 5D:
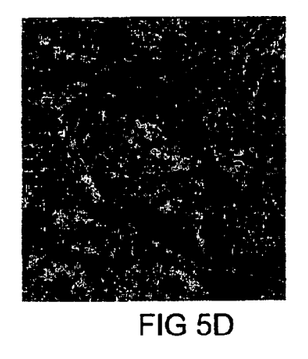

Therefore, the different convergences between different kinds of color are important. FIGS. 4a and 4b show examples of the different images for colon cancer. FIGS. 5a through 5d show examples of the different images for a breast cancer cell.

The embodiment describes only two different single spectrum images, but other embodiments may use a different luminance convert step 130 which uses a plurality of different single spectrum images, or some kind of combined single spectrum image which is combined by transforming and weighting the number of different images together.

The general structure and techniques, and more specific embodiments which can be used to effect different ways of carrying out the more general goals are described herein.

Although only a few embodiments have been disclosed in detail above, other embodiments are possible and the inventor(s) intend these to be encompassed within this specification. The specification describes specific examples to accomplish a more general goal that may be accomplished in another way. This disclosure is intended to be exemplary and the claims are intended to cover any modification or alternative which might be predictable to a person having ordinary skill in the art. For example, other stains and colors may be used. Other single spectrum images, or images that are multispectrum or narrow spectrum can also be used. Moreover, when specific values, such as 420 nm, are given herein, those specific values are intended to be center values within a range of 10-20%, for example.

Also, the inventor intends that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The computer may be a Pentium class computer, running Windows XP or Linux, or may be a Macintosh computer. The computer may also be a handheld computer, such as a PDA, cellphone, or laptop.

The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

What is claimed is:

1. A method of enhancing a digital image, comprising:
   using a multi-spectral imaging system to obtain a first digital image comprising a microscope image indicative of a sample, and a second digital image indicative of the same sample but which covers substantially only a single spectrum;
   dividing the first digital image into component parts indicative of the first digital image;
   dividing the second digital image into component parts indicative of the second digital image; and
   enhancing the image quality of the first digital image by replacing one of the component parts of the first digital image with a corresponding component part of the second digital image.

2. The method of claim 1, wherein the corresponding component part from the second digital image is a luminance component from the second digital image which is used to replace a luminance component in the first digital image.

3. The method of claim 1, further comprising converting each of the first digital image and the second digital image into a first device independent color space, wherein the step of dividing the first digital image into component parts indicative of the first digital image comprises separating the first digital image into a plurality of channels in the device independent color space, wherein the step of dividing the second digital image into component parts indicative of the second digital image comprises separating the second digital image into a plurality of channels in the device independent color space, and wherein the step of replacing one of the component parts of the first digital image with a corresponding component part of the second digital image comprises replacing one of the plurality of channels in the first digital image with a corresponding one of the plurality of channels from the second digital image.

4. The method of claim 3, wherein the device independent color space is an L*a*b* color space.

5. The method of claim 3, further comprising combining, after the replacing step, the channels of the first digital image to form a new image, and transforming the new image to a different color space.

6. The method of claim 1, wherein the second digital image is at substantially 420 nm.

7. The method of claim 1, wherein the second digital image is at 720 nm.

8. A method of enhancing a digital image, comprising:
using a multi-spectral imaging system to obtain a first image indicative of full color image of a magnified sample, and to obtain a second image indicative of a single spectrum image of the same magnified sample;
converting each of the first and second images into a device independent color space;
separating each of the first and second images in the device independent color space into a plurality of channels; and
replacing a corresponding channel of the first image with a channel from the second image to enhance a quality of the first image; and creating a new image based on the channels of the first image, and the channel of the second image.

* * * * *

UNITED STATES PATENT AND TRADEMARK OFFICE
CERTIFICATE OF CORRECTION

PATENT NO. : 8,817,040 B2
APPLICATION NO. : 12/454711
DATED : August 26, 2014
INVENTOR(S) : Roscoe Atkinson

It is certified that error appears in the above-identified patent and that said Letters Patent is hereby corrected as shown below:

On the title page

Page 2, item (56) US Patent Document, Column 2:
Delete "6,499,690 B1 12/2002 Katayama et al." and insert --6,466,690 B2 10/2002 Bacus et al.--

Page 2, item (56) US Patent Document, Column 2:
Delete "6,553,135 B1 4/2003 Ring et al." and insert --6,553,135 B1 4/2003 Douglass et al.--

Signed and Sealed this
Eighth Day of March, 2016

Michelle K. Lee
*Director of the United States Patent and Trademark Office*